(12) United States Patent
Gutman et al.

(10) Patent No.: US 7,765,109 B2
(45) Date of Patent: Jul. 27, 2010

(54) SYSTEMS AND METHODS FOR OBTAINING READINGS OF DIAGNOSTIC IMAGING STUDIES

(75) Inventors: Abraham Gutman, Chestnut Hill, MA (US); Michael Goldner, Natick, MA (US)

(73) Assignee: AG Mednet, Inc., Boston, MA (US)

( * ) Notice: Subject to any disclaimer, the term of this patent is extended or adjusted under 35 U.S.C. 154(b) by 1079 days.

(21) Appl. No.: 11/334,919

(22) Filed: Jan. 19, 2006

(65) Prior Publication Data

US 2007/0225921 A1    Sep. 27, 2007

(51) Int. Cl.
 *G06Q 10/00*    (2006.01)
(52) U.S. Cl. .................. 705/2; 705/3; 705/4; 705/37; 600/300; 600/301
(58) Field of Classification Search .................. 705/2–4; 600/300–301
See application file for complete search history.

(56) References Cited

U.S. PATENT DOCUMENTS

| 5,469,353 | A |   | 11/1995 | Pinsky et al. ........... 364/413.01 |
| 6,006,191 | A | * | 12/1999 | DiRienzo ........................ 705/2 |
| 6,557,102 | B1 |  | 4/2003 | Wong et al. .................. 713/176 |
| 6,574,629 | B1 |  | 6/2003 | Cooke, Jr. et al. ............. 707/10 |
| 6,574,742 | B1 | * | 6/2003 | Jamroga et al. ............. 713/400 |
| 6,678,703 | B2 |  | 1/2004 | Rothschild et al. ........... 707/201 |
| 2002/0184325 | A1 |  | 12/2002 | Killcommons et al. ....... 709/206 |
| 2003/0126279 | A1 |  | 7/2003 | Hu et al. ...................... 709/233 |
| 2003/0195838 | A1 | * | 10/2003 | Henley ......................... 705/37 |
| 2004/0061889 | A1 |  | 4/2004 | Wood et al. ................. 358/1.15 |
| 2005/0114380 | A1 |  | 5/2005 | Eldar et al. .................. 707/102 |
| 2006/0116902 | A1 |  | 6/2006 | Amador et al. ................. 705/2 |
| 2007/0127790 | A1 |  | 6/2007 | Lau et al. ..................... 382/128 |
| 2007/0223793 | A1 |  | 9/2007 | Gutman ...................... 382/128 |

OTHER PUBLICATIONS

"Automated Examination Notification of Emergency Department Images in a Picture Archiving and Communication System," Andriole et al., Journal of Digital Imaging, vol. 14, No. 2, Suppl 1 Jun. 2001: pp. 143-144.t.*
Printout of website of Neurostar Solutions; Virtual Radiology Network (VRN) (Jan, 18, 2006).
Desacc, Inc. DICOMgateway™ 1.1, *Rule Based Dicom Routing*, http//www.desacc.com, 2 pp.

* cited by examiner

*Primary Examiner*—Vivek D Koppikar
(74) *Attorney, Agent, or Firm*—Sunstein Kann Murphy & Timbers LLP

(57) ABSTRACT

Systems and methods for method providing a diagnostic image study to one or more interpreters may include receiving the diagnostic image study at a first translator, making the diagnostic image study available to one or more board certified and credentialed interpreters substantially simultaneously, and selecting one or more of the interpreters to provide an interpretation of the images based on one or more variables.

15 Claims, 2 Drawing Sheets

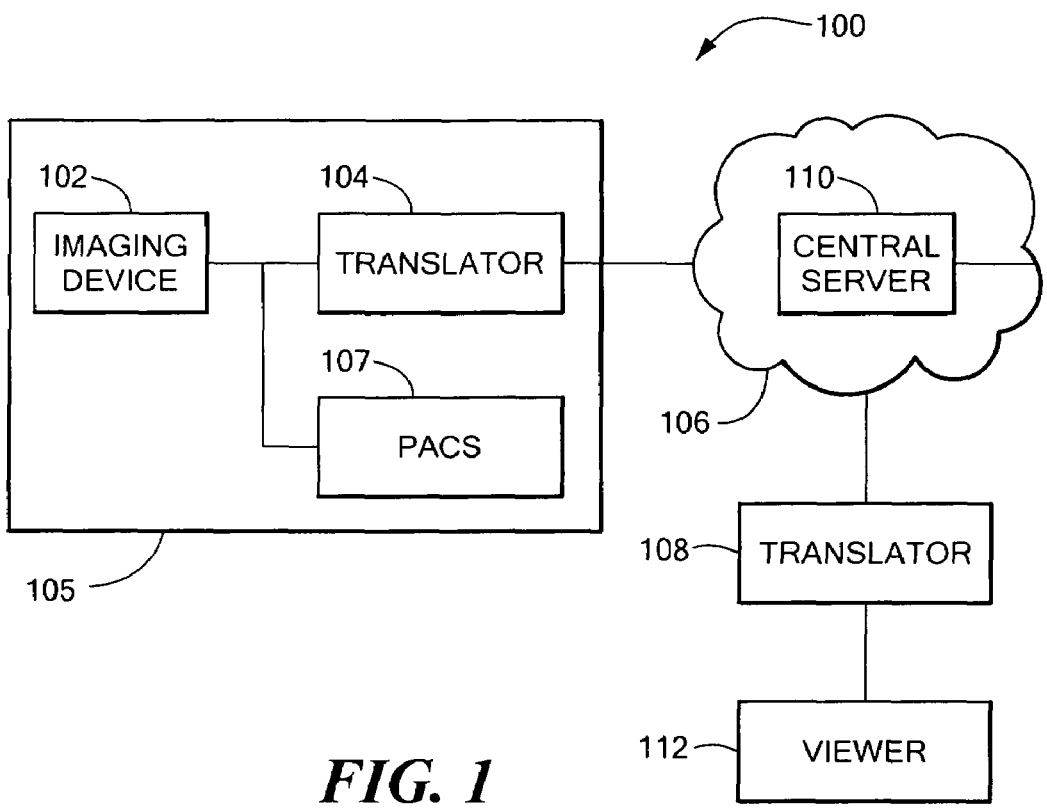
*FIG. 1*
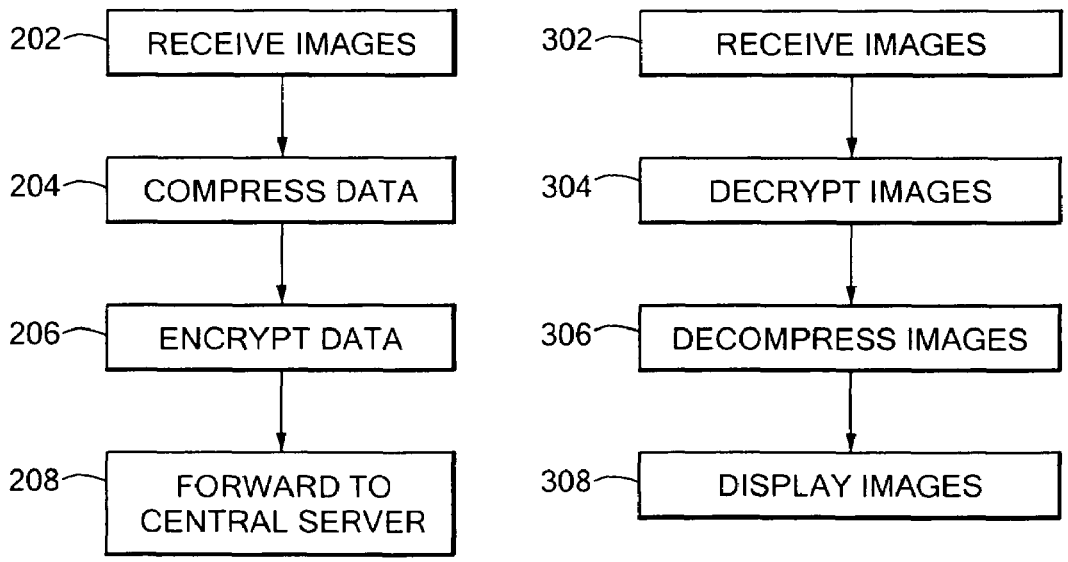
*FIG. 2*  *FIG. 3*

SYSTEMS AND METHODS FOR OBTAINING READINGS OF DIAGNOSTIC IMAGING STUDIES

CROSS REFERENCE TO RELATED APPLICATIONS

This application is related to U.S. patent application Ser. No. 11/335,244, entitled Systems And Methods For Providing Diagnostic Imaging Studies To Remote Users, filed on even date herewith.

TECHNICAL FIELD AND BACKGROUND ART

The present invention relates to the transport and distribution of diagnostics image studies and, in particular, to systems and methods for obtaining readings of diagnostic images from interpreters in locations remote from where the diagnostic images were created.

It is known in the prior art to utilize the Digital Imaging in Communication and Medicine (DICOM) standard to electronically transfer diagnostic imaging studies from a modality or PACS (Picture Archiving and Communications System) (both of which may be referred to as an "imaging device" herein) to a remote user. Examples of modalities include CAT scanners, X-ray machines, and MRI machines. The output of these devices may be referred to herein as a "diagnostic imaging study". In many cases the diagnostic imaging study will include one or more images. In many cases, the diagnostic imaging study will contain several images.

Many operators of imaging devices may experience difficulties in ensuring timely and competent interpretations of imaging studies. These difficulties may arise from many different sources. For example, the imaging device operator may create more studies than may be interpreted by on location interpreters. That is, the interpreters that are located at the operator of the imaging device (e.g., a hospital) may not have the time to return interpretations in a timely manner.

Delays in receiving an interpretation may effect the profitability of an operator of an imaging device. This effect may come from billing requirements imposed upon the operator of the modality. In particular, the operator is not allowed to charge for a procedure until a final interpretation of the images has been completed. A final interpretation may only be made using diagnostic quality images, i.e., where the images being interpreted essentially are an exact facsimile of the images output by the modality, without any change in resolution.

In addition, the costs associated with hiring additional interpreters (e.g., radiologists) may exceed the budget of a particular image operator. For instance, a small hospital in a relatively unpopulated area may not have the resources or the demand to hire a full time specialist to interpret images. The small hospital, however, may still need, for time to time, to have interpretations done on imaging studies.

Furthermore, some interpreters at one location may have free time that they could devote to interpreting imaging studies from other locations.

SUMMARY OF THE INVENTION

Embodiments of the present invention may solve one or more of the above mentioned limitations of the prior art. For instance, embodiments of the present invention may allow operators of imaging devices to make a particular imaging study available to one or more interpreters that may be located in a location remote from the operators. In addition, some embodiments may allow for interpreters to place "bids" on the interpretations. Bidding could include price, time of interpretation or any other requirement. For instance, if multiple interpreters are simultaneously presented with a imaging study, the first to respond may provide interpretation. In another example, the interpreter that offers to provide the interpretation for the lowest amount may be awarded the interpretation. In this manner, operators of imaging devices may be able to receive more timely or more cost efficient (or both) interpretations of medical imaging studies.

BRIEF DESCRIPTION OF THE DRAWINGS

The foregoing features of the invention will be more readily understood by reference to the following detailed description, taken with reference to the accompanying drawings, in which:

FIG. 1 is an example of a system on which embodiments of the present invention may be implemented;

FIG. 2 is a flowchart showing one embodiment of the process that occurs in the translator;

FIG. 3 shows an embodiment of the operations that may be performed in the second translator;

DETAILED DESCRIPTION OF SPECIFIC EMBODIMENTS

Figure 4:
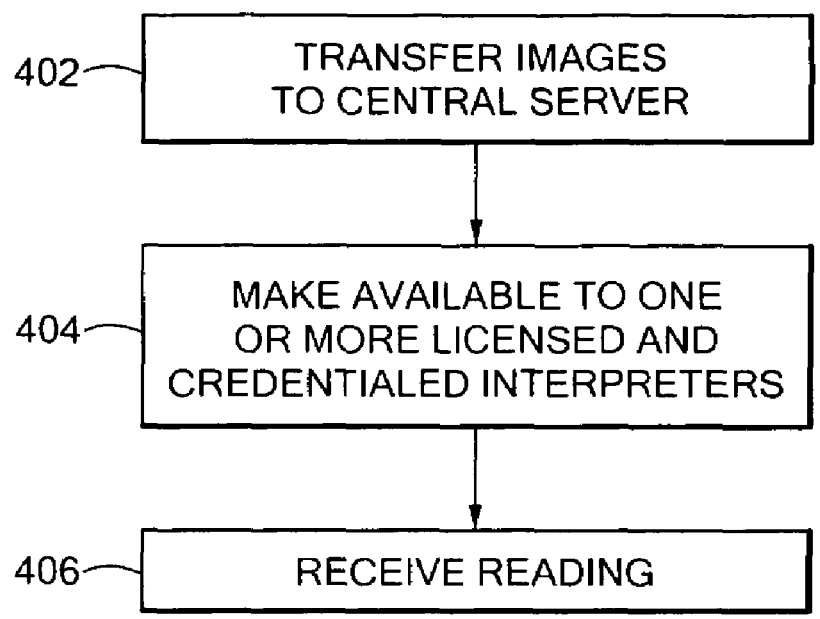
FIG. 4 is a flow diagram showing one embodiment of distributing image data.

Referring now to FIG. 1, in some embodiments of the present invention, the system 100 may include imaging device 102. Of course, an imaging device is not required and the system may receive images from any source. This imaging device 102 may be any type of modality that may take diagnostic images of a patient. For example, the imaging device 102 may be an MRI machine, a digital X-ray machine, a CAT scan machine or any other type device. In other embodiments, the imaging device 102 may be any type of imaging device whether or not it is used for a diagnostic image of the human or not. For instance, the imaging device 102 could be an electron microscope or the like. The imaging device 102 transfers the images to other devices in the internal network 105 at the location where the imaging device 102 is located. For instance the internal network 105 could be a local area network (LAN) that has a plurality of devices connected to it. For instance, the imaging device 102 could be connected via the internal network 105 to a translator 104 and a PACS 107. As shown the network is connected to a PACS 107. Of course, this element is optional and could be omitted or other elements could be coupled to the network 105, or the imaging device 102 could transfer the diagnostic imaging study to a PACS 107 which in turn transfers it to the translator 104.

Typically, an imaging device 102 will transfer the information, via the DICOM standard. As is well known, the DICOM standard requires that while a transfer is occurring, the systems at both ends need to be part of the transaction, and must be there throughout the transaction. The transfer transactions (DICOM push/pull) are very detailed and require interaction of the systems for each study image being transmitted. In addition, the DICOM standard requires that the imaging device provide all of the images to whatever destination is selected. If an imaging device is attempting to send the pictures/images to a remote site, the transportation of the images may tie up the imaging device for a substantial amount of time if the connection between the external device and the imaging device 102 is not robust. That is, if the imaging device 102 cannot get confirmation that each and every image was transferred to the receiving device, the imaging device may not move on to the next procedure until all of those images are transferred. This, in turn, may lead to delays in the operation of the imaging device and therefore increase the time of patient care and, possibly, reduce the profitability of imaging device 102 because the profitability of such of a device increases as the number of studies may increase.

In the system 100 as shown in FIG. 1 some of these problems may be substantially reduced. For instance, the imaging device 102 is connected through a local area network, in some embodiments, to a translator 104 as well as a PACS 107.

The translator 104, in one embodiment, compresses the stream of diagnostic imaging data, as well as any data associated therewith and then encrypts the data. In preferred embodiment, the compression is lossless.

The translator 104 may include a central processing unit (CPU) having a conventional microprocessor, random access memory (RAM) for temporary storage of information, and read only memory (ROM) for permanent storage of read only information. A memory controller is provided for controlling system RAM. In one embodiment, the translator 104 does not store any data to memory until it is encrypted regardless of whether it has been compressed.

Mass storage may be provided by known non-volatile storage media, such as a, a digital versatile disk (not shown), a CD-ROM, or a hard disk. Data and software may be exchanged with the translator 104 via removable media, such as a diskette or a CD-ROM or be downloaded via the internet or other connective network.

The translator 104 system preferably is controlled and coordinated by operating system software such as Linux or DOS. Among other computer system control functions, the operating system controls allocation of system resources and performs tasks such as process scheduling, memory management, networking, and I/O services.

A network adapter also may be included to enable the translator 104 to be interconnected to a network, such as the internet 106 and LAN 105 or a dedicated wide area network. The network, which may be a local area network (LAN), a wide area network (WAN), or the Internet, may utilize general purpose communication lines that interconnect a plurality of network devices.

After compression and encryption are completed, the images, in one embodiment, may be forwarded to the central server 110 to which the translator may connect through the Internet 106 or through a private network. In an illustrative embodiment, an operator of the imaging device 102 will select which doctors or other interpreters may have access to the images in a particular study. That information dictates where and how the information is stored in the central server 110. For instance, each doctor may have an account at the central server 110, or each file may be encrypted in such a manner that only particular doctors who are authorized to see the images may access the information on the central server 110. Advantageously, because the information is now compressed and encrypted in such a way as to make it possible to transport it using protocols other than DICOM, the information is no longer subject to the DICOM requirements of image by image protocol. Therefore, doctors may have access to the diagnostic quality images much more quickly, and more doctors can have access to the information in a completely flexible manner. In one embodiment, the translator may direct the central server (based on information received with the diagnostic imaging study) where the study should be further sent without the need for any intervention from the recipient(s) to whom the study was sent.

The system may also include an additional translator 108, which decrypts and decompresses the information before it is viewed by the device 112 (referred to herein as a viewer) used by the interpreter to view the images associated with the diagnostic imaging study. This additional translator 108 should be able to decrypt the data and then decompress the data such that a perfectly lossless representation of the original DICOM compliant data is delivered to the viewer by the additional translator 108. As such, any viewer 112 or any PACS will be able to display the study. This allows for the many heterogeneous machines such as modalities or PACS from different vendors to effectively communicate without any involvement from the vendors or original manufacturers of the modalities or PACS's. In one embodiment, the additional translator 108 may have the same or similar to capabilities as the translator 104 and vice-versa.

FIG. 2 is a flowchart showing one embodiment the process that occurs in the translator 104. As shown, the process includes steps performed in a specific order and includes a specific number of steps. One of ordinary skill should readily realize that certain steps may be omitted, certain steps may be added, and/or certain steps may be performed in an order that is different from that shown in FIG. 2 (or another flow chart shown herein) without departing from the present invention.

As shown in FIG. 2, the process begins at step 202 where the transmitter 104 receives images from the modality 102. The images may be received in any manner but, typically, they are received via the DICOM protocol. As such, the process of receiving the images, in some embodiments, requires complying with all of the regulations imposed upon DICOM and HIPAA (Health Insurance Portability and Accountability Act of 1996). However, because the translator 104 is located on the same internal network 105 as the imaging device 102 this transfer may be very fast as compared to point-to-point image transmission to a remote location.

After the images are received at step 202, they are then compressed at step 204. In some embodiments, the compression may begin before the entire study is received. In other embodiments, the compression may not begin until the entire has been received. Regardless of when compression begins, in an illustrative embodiment, the images as well as any meta-data associated therewith may be compressed, for example, utilizing a "bitwise" compression scheme. Bitwise compression is well known in the art and may generally be described as applying bitwise logical operators to a strings of bits to create a compressed version of the original string independent of how these strings may be interpreted by any computer software. In one embodiment, the compression may be lossless compression. Of course, other types of compression could be used and are within the scope of the present invention.

After the information is compressed in step 204, the data is then encrypted in step 206. In one embodiment, the data is encrypted using an Asymmetrical Encryption System (AES). In such an embodiment, preferably 128-bit encryption is used. Of course, other types of encryption may also be used.

In one embodiment, the operator of the imaging device 102 may be allowed to select certain doctors (or group(s) of doctors) that may view or may be sent the particular study. In such a case, the translator 104 may also encrypt the key to the data using a particular individual or groups public/private pair, thus ensuring that only those individuals may view the study.

This aspect may be important to the distribution of studies to certified and accredited doctors as described in further detail below.

After steps 204 and 206 are completed, in one embodiment, the information is stored to a hard drive of the translator 104. Preferably, no data is ever stored to the hard drive of the translator 104 until is has been encrypted, thus, even if the translator is misplaced or otherwise unaccounted for, patient information will not be readily available to anyone other than those who were supposed to access to the information. In other embodiments, the information is not stored to the hard drive of the translator 104 but, rather, is immediately sent to another location, such as the central server 110.

Regardless of whether the information is stored to the hard drive, after encryption (and preferably after lossless compression) the information may then be forwarded to the central server 110 via, for instance, the Internet 106. The information having been translated may be transferred in any manner (e.g., via a packet based connection) to the central server 110 rather than the previously used and cumbersome DICOM protocol. The central server 110 may interpret the information that is received and forward the study to specific doctors to whom the operator of the imaging device 102 has previously selected. In this manner, the system may allow for simultaneous point (the imaging device or PACS) to multi-point (multiple individuals) distribution of diagnostic images.

To ensure safety and privacy, as well as to comply with HIPAA, the data (or the key to the data) may be further encrypted using the doctor's public/private key. Of course, many other methods of ensuring safety may be implemented and anything that will ensure the compliance with HIPAA is preferred.

Of course, the reverse of steps 204 and 206 may be completed in the second translator 108 as shown in FIG. 3. For instance, the second translator 108 could decrypt and decompress the data so that all the images of a particular study could be displayed on a viewer 112, for example.

FIG. 3 shows an embodiment of the operations that may be performed in the second translator 108. The process includes a step of receiving the encrypted and compressed images at step 302. In one embodiment, the images may be received from a central server 110. In other embodiments, the images may be received from another location such as, for example, a PACS or an imaging device. The images are then decrypted at step 304 and then decompressed at step 306. As one of ordinary skill in the art will readily realize, many types of decompression and decryption techniques may be used. Finally, the images may be displayed, for example, on a viewer 112 at step 308.

The foregoing discussion has provided an example of systems and methods that may allow diagnostic quality images to be transferred from a modality to one or more individuals. This system, and others, may create a platform from which an operator of an imaging device may make available to one or more remote diagnostic image interpreters (for example, doctors, radiologists, cardiologists, or other professionals qualified to interpret diagnostic images) in a safe and efficient manner. In an illustrative embodiment, the images may be made available to interpreters that have been licensed and credentialed to interpret images transmitted by the operator of the imaging device. For example, the images may be transferred to a radiologist that is remote from a hospital when the hospital needs an interpretation of a study (or other collection of images) in a expedited manner but does not have available on-site human resources to accomplish the task. Additionally, this may allow a particular hospital to expand its access to interpreting physicians who also have a translator, while also allowing a single interpreting physician to provide interpretations to several different hospitals, which also have a translator on site.

FIG. 4 is a flow diagram showing one embodiment of distributing image data. In general, FIG. 4 shows steps by which diagnostic images may be distributed to one or more interpreters. At step 402, the images that constitute a study (one or images) are transferred from an imaging device 102 to a central server. For example, and as discussed above, the images could be transferred, after being compressed and encrypted to the central server 110 shown in FIG. 1. Of course, the images need not be either encrypted or compressed. The images are then made available to one or more licensed and credentialed interpreters at step 404. In order for an interpreter to receive the images, under current law, the interpreter must be licensed to practice medicine (for example, by the state medical licensing board) in the state where the studies were created. Also under current law, the interpreter needs to be credentialed by the operator of the imaging device (for example, a hospital or other health care provider) to provide diagnoses related to the study. Of course, if the law were to change, then, possibly, the interpreter would not need to be either credentialed or licensed or either.

Figure 5:
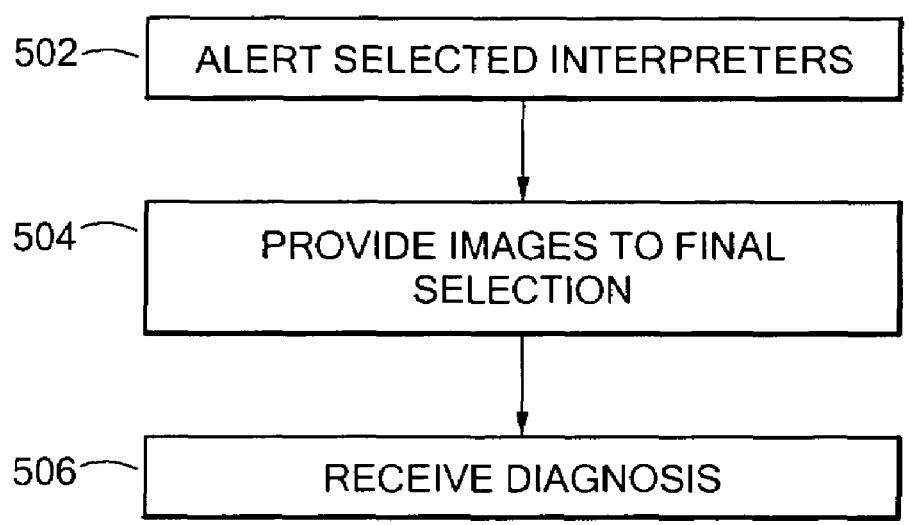
FIG. 5 is a flow diagram by which the operator of an imaging device may get one or more interpretations of a study.

FIG. 5 is a flow diagram by which the operator of an imaging device may get one or more interpretations of a study. In one embodiment, the method shown in this flow diagram may facilitate the more timely and cost effective interpretation of diagnostic images. This may be achieved, for example, by allowing licensed and credentialed interpreters to have a marketplace bid on "contracts" to perform diagnostic interpretations. Such a marketplace may reduce the time for receiving interpretations of diagnostic images. In addition, such a marketplace may also reduce the cost of such readings. For example, rather than having to have an interpreter on staff at a particular imaging center, the imaging center could only pay for the interpretations that it needs. This may be especially beneficial in locations where it may be hard to recruit qualified individuals, or where the cost employing such an individual is too high.

The process begins at step 502 where interpreters that have been selected by the operator of the imaging device are alerted that a diagnostic interpretation is needed. This may be done in any manner. For instance, the interpreter may have an account at, for example, a central server that causes a notification (such as an e-mail, a fax, a page, an instant message or any other means of alerting the interpreter). Of course, the operator of the imaging device may have selected the one or more interpreters from a list of licensed and credentialed interpreters with which the operator has an existing relationship. In some embodiments, the alert may be represented as a possible interpretation placed on a message board accessible by at least the selected persons, or at a location of the doctor who referred the patient to the operator of the imaging device.

The images may be provided to the final selected interpreter at step 504. An interpreter may become the final selected interpreter in at least the following ways: the interpreter that first responds the desire and ability to perform the interpretation is selected; the interpreter that offers the lowest price may be selected; the interpreter that offers the quickest response may be selected. Of course, other criteria may also be used to determine the final selected interpreter. For example, the criteria may include: sub-specialty, years of experience, physical location, availability to the interpreter of specialized hardware or software, and number of previous interpretations by the interpreter.

The diagnosis (or final read) is then received at step 506. The diagnosis could be received at any number of locations.

For instance, the diagnosis could be received at a central server or at a location of the operator of an imaging device.

What is claimed is:

1. A method of providing a diagnostic image study to one or more interpreters comprising:
   receiving the diagnostic image study at a first translator computer;
   using a central server to route the diagnostic image study to a plurality of board certified and credentialed interpreters substantially simultaneously;
   using the central server to notify via an alert, a plurality of available board certified and credentialed interpreters of the need for an interpretation of the diagnostic image study;
   allowing responses of the interpreters;
   selecting an interpreter based upon the selected interpreter being the first to respond and having the desire and ability to perform the interpretation.

2. A method according to claim 1, wherein the first translator compresses and encrypts the diagnostic imaging study before the study is made available to the one or more interpreters.

3. A method according to claim 2, wherein the first translator performs bit wise compression on the diagnostic image study.

4. A method according to claim 1, wherein the diagnostic image study is made available to the one or more interpreters by transferring the diagnostic image study to a central server.

5. A method according to claim 4, wherein the central server is connected to the Internet.

6. A method according to claim 1, wherein the step of selecting is based upon one or more of the following additional variables: the cost for the interpretation, sub-specialty, years of experience, physical location, availability to the interpreter of specialized hardware or software, and number of previous interpretations by the interpreter.

7. A method according to claim 1, wherein the study is routed losslessly.

8. A method according to claim 1, wherein the study is encrypted by the translator and stored only in encrypted form.

9. A method according to claim 1, wherein the study is routed to at least one interpreter translator.

10. A method according to claim 1, wherein the study is transmitted from the translator to the central server via a packet based transmission protocol.

11. A method according to claim 1, wherein the study is transmitted from the translator to the central server using a transmission protocol other than DICOM.

12. A method according to claim 2, wherein the first translator encrypts the study using one or more keys corresponding to one or more selected interpreters so that the study may only be de-encrypted by the corresponding one or more interpreters.

13. A method according to claim 1, comprising selecting more than one interpreter and using the central server to route the diagnostic image study to the selected interpreters.

14. A method according to claim 12, wherein the first translator encrypts using an asymmetrical encryption system.

15. A method according claim 14, wherein the asymmetric encryptions system uses public-private key encryption.

* * * * *